United States Patent
Minks

(10) Patent No.: US 7,601,707 B1
(45) Date of Patent: Oct. 13, 2009

(54) METHOD FOR INSTANTLY RELIEVING TISSUE INFLAMMATION

(76) Inventor: William J. Minks, 2751 Skeies Dr., Des Moines, IA (US) 50317

( * ) Notice: Subject to any disclaimer, the term of this patent is extended or adjusted under 35 U.S.C. 154(b) by 847 days.

(21) Appl. No.: 10/794,593

(22) Filed: Mar. 5, 2004

Related U.S. Application Data

(60) Provisional application No. 60/452,426, filed on Mar. 5, 2003.

(51) Int. Cl.
*A61K 31/56* (2006.01)
(52) U.S. Cl. ........................ 514/170; 514/171
(58) Field of Classification Search .................. 514/170, 514/171
See application file for complete search history.

(56) References Cited

U.S. PATENT DOCUMENTS 4,312,865 A * 1/1982 Szucs .......................... 514/180

5,478,315 A * 12/1995 Brothers et al. ............. 604/115

FOREIGN PATENT DOCUMENTS

CN 1092987 * 10/1994

* cited by examiner

*Primary Examiner*—San-ming Hui
(74) *Attorney, Agent, or Firm*—Patent Law Group LLP; David C. Hsia

(57) ABSTRACT

A method for treating an inflamed tissue includes locally applying a solution comprising a corticosteroid and an anesthetic agent to the inflamed tissue so that the solution directly contacts the inflamed tissue. The corticosteroid may be a 4 mg/ml dexamethasone solution and the anesthetic agent may be a 1% lidocaine solution. The dexamethasone solution and the lidocaine solution may be mixed in a 1 to 3 ratio. Locally applying the solution may include penetrating the skin with a hypodermic needle, directing the hypodermic needle parallel to and past the inflamed tissue, and while withdrawing the hypodermic needle, spraying the solution directly onto the surface of the inflamed tissue.

10 Claims, 13 Drawing Sheets

VENTRAL VIEW

RADIAL SIDE          THUMB

ULNAR SIDE          PINKY FINGER SIDE

1. - BRACHIORADIALIS
2. - PROHSTOR TERES
3. - FLEXOR CARP; RADIALIS
4. - SLIP FROM THE CORACOID PROCESS OF THE ULNA
5. - FLEXOR POLLICIS LONGUS
6. - ADDUCTOR POLLICIS LONGUS

Transverse section across distal ends of radius and ulna.

METHOD FOR INSTANTLY RELIEVING TISSUE INFLAMMATION

CROSS-REFERENCE TO RELATED APPLICATIONS

This application claims the benefit of U.S. Provisional Application No. 60/452,426, filed Mar. 5, 2003, which is incorporated herein by this reference.

FIELD OF INVENTION

This invention relates to a method for treating inflammation.

DESCRIPTION OF RELATED ART

Inflammatory conditions, afflictions, illnesses, and diseases include but are not limited to: (1) all varieties of dermatitis, seborrhea, psoriasis, eczema, and allergic; (2) subcutaneous inflammatory conditions including tendonitis, myositis, fasciitis, neuritis, arthritis, arteritis, phlebitis, and back pain—especially back pain associated with inflammatory nodules; (3) repetitive strain injuries (RSIs) including cumulative trauma disorders, tendonitis, Raynaud's syndrome and phenomena, the tunnel syndromes, and reflex sympathetic dystrophy; (4) collagen vascular diseases including Systemic lupus erythematosis, rheumatoid arthritis, dermatomyositis, scleroderma, and polyarteritis nodosa; (5) pulmonitis, myocarditis, pericarditis, mediastinitis, peritonitis, pancreatitis, gastritis, hepatitis, cholecystitis, nephritis, cystitis, urethritis, temporal-mandibular joint (TMJ) problems or disease and some forms of cancer including lymphoma and inflammatory breast carcinoma; (6) trauma victims, multiple sclerosis, amyotrophic lateral sclerosis, and burn victims.

The word inflammation comes from the Latin words inflammatio and inflammare, which means to set on fire. Inflammation is the condition that tissues enter as a reaction to injury, or the body's response to injury. Inflammation consists of the presence of inflammatory cells, consisting predominantly of polymorphonucleocytes in acute inflammation and lymphocytes in chronic inflammation, accompanied by a variety of other cell types including macrophages. Changes seen under the microscope include hyperemia, stasis, changes in the blood and walls of the small vessels, and by various exudations. The presence of inflammation is accompanied by clinical findings of pain, heat, redness, swelling, tenderness and loss of function.

When an injury occurs, for example to a tendon, there are microscopic tears and bleeding. A number of chemicals are released, such as bradykins, systokinins, slow reacting substance, leukotrenes, prostaglandins, and chemotactic factors. Cell walls become unstable and easier to phagocytize (i.e., ingest) by phagocytes, such as the polymorphonucleocyte, macrophages, killer B-lymphocytes, and monocytes. These cells are the more general phagocytes. Giant cells are phagocytes that specialize and are seen in foreign body reactions, granulomas (e.g., TB and fungal infections), and some types of viral infections (e.g., Herpes).

Inflammation is accompanied by a discharge, which is characterized as an exudate or transudate according to its viscosity and composition.

There are several types of inflammation, including:

Acute inflammation, the inflammatory processes are active, and polymorphonucleocytes or neutrophils predominate.

Adhesive inflammation promotes the adhesion of contiguous surfaces.

Atrophic inflammation results in atrophy and deformity.

Catarrhal inflammation affects principally a mucous surface and which is marked by a discharge of mucous and epithelial debris, for instance, a runny nose.

Chronic inflammation is a slow progress and marked by the formation of new connective tissue.

Cirrhotic inflammation is similar to atrophic inflammation.

Croupous inflammation is a fibrinous inflammation leading to the formation of a false membrane.

Diffuse inflammation is inflammation that is both interstitial and parenchymatous or is spread over a large area.

Disseminated inflammation has a number of distinct foci.

Exudative inflammation is when the prominent feature is an exudate.

Fibrinous inflammation is characterized by an exudate of coagulated fibrin.

Fibroid inflammation is similar to atrophic inflammation.

Focal inflammation is confined to a single spot or to a few limited spots.

Granulomatous inflammation is chronic inflammation in which there is a formation of granulation tissue.

Hyperplastic inflammation leads to the formation of new connective tissue fibers.

Hypertrophic inflammation is inflammation, which is marked by increase in the size of the elements composing the affected tissue.

Interstitial inflammation primarily affects the stroma of an organ.

Metastatic inflammation is inflammation that is reproduced in a distant body part by the transport of infectious, chemical, or cancerous material through the blood vessels and lymph organs.

Necrotic inflammation is attended by the death of the affected tissue.

Obliterative inflammation affects the lining membrane of a cavity or vessel, producing adhesions between the surfaces and consequent obliteration of the lumen.

Parenchymatous inflammation primarily affects the essential tissue elements of an organ.

Plastic, productive, and proliferous inflammation is synonyms for hyperplastic inflammation.

Reactive inflammation occurs around a foreign body or a focus of degeneration.

Sclerosing inflammation is similar to atrophic inflammation except that more scarring is implied.

Seroplastic inflammation is accompanied by both serous and plastic exudation.

Serous inflammation produces an exudation of serum.

Simple inflammation is when there is no flow of pus or other product of inflammation.

Specific inflammation is due to a particular microorganism.

Suppurative inflammation is characterized by the formation of pus.

Toxic inflammation is caused by a poison, such as a bacterial product.

Traumatic inflammation is caused by an injury.

Inflammation should be reduced or eliminated because it causes damage to the body part affected. Inflammation is designed to keep us from being invaded by microorganisms. It is the body's last-ditch effort to protect itself from invading microbes. Until the advent of antibiotics, inflammation was the best strategy against infection. Because of the advancements in medicine in controlling the causes of injury, the scenario of inflammation doing more harm than good is more and more common.

Inflammation is not very discriminating. Inflammation affects the targeted tissue's near-by blood vessels and nerves, resulting in clotted, clogged vessels and invasion and irritation of nerves, which results in cold areas distal to the inflamed area, and burning, neuropathic pain. Inflammation can lead to a vicious cycle of injury, release of inflammatory chemicals, attraction of more inflammatory cells, which gives more injury. Inflammation leads to scarring. Scar tissue has limited function. Scarring impairs the function of normal tissues near it. Scars can be painful. If the cause of the injury can be controlled, it is prudent to suppress inflammation when possible.

Thus, what is needed is a method to effectively and quickly treat inflammation.

BRIEF DESCRIPTION OF THE DRAWINGS

Use of the same reference numbers in different figures indicates similar or identical elements.

SUMMARY

Figure 1:
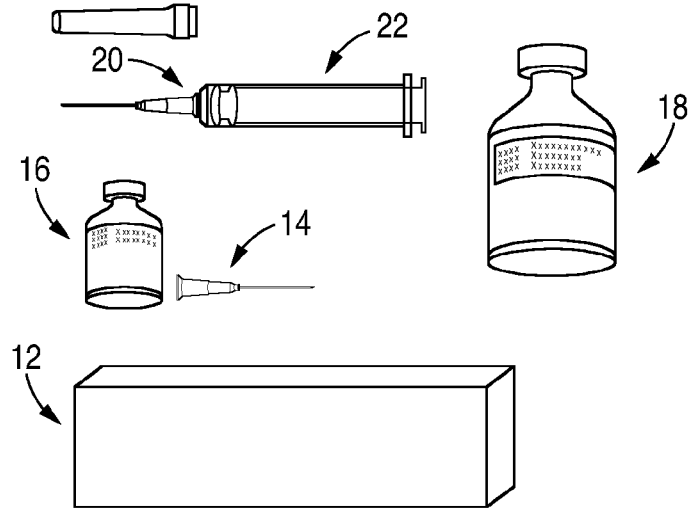
FIG. 1 illustrates materials to be used in a method for treating inflamed tissues in one embodiment of the invention.

In one embodiment of the invention, a method for treating an inflamed tissue includes locally applying a solution comprising a corticosteroid and an anesthetic agent to the inflamed tissue so that the solution directly contacts the inflamed tissue. The corticosteroid may be a 4 mg/ml dexamethasone solution and the anesthetic agent may be a 1% lidocaine solution. The dexamethasone solution and the lidocaine solution may be mixed in a 1 to 3 ratio. Locally applying the solution may include penetrating the skin with a hypodermic needle, directing the hypodermic needle parallel to and past the inflamed tissue, and while withdrawing the hypodermic needle, spraying the solution directly onto the surface of the inflamed tissue.

DETAILED DESCRIPTION

Introduction to the Method

A method is provided to instantly relieve the signs and symptoms of inflammation, thereby restoring normal bodily function. The method consists of direct local application of a combination of medicines to an inflamed tissue. The combination of medicines halts the inflammatory process and its accompanying symptoms. The method takes advantage of a previously unrecognized synergistic, supra additive effect of the combined medicines. Delivery can be accomplished with any system that can locally apply the combination of medicines directly onto the inflamed area.

The method described herein is curative, palliative, or beneficial for any biologic, medical, or veterinary condition, affliction, illness, or disease that is acute, sub-acute, or chronic and involves inflammation or pathologic muscle contraction, either external or internal. The method can be applied to any condition, affliction, illness, or disease that ends with the suffix "itis" or has the clinical signs and symptoms of inflammation including heat, redness, pain and swelling, or laboratory evidence of inflammation (e.g., elevated erythrocyte sedimentation rates or C-reactive proteins), or histological or pathological appearance of inflammation under microscopy.

The combination of medicines also has previously undiscovered muscle relaxant properties. Based on these properties, the combination of medicine is also useful for headache, neck, shoulder, and back problems or any other conditions with a muscle contraction component.

Advantages of the Method Compared to Currently Available Treatment Options

The method described herein is more effective than current treatments. For instance, RSI (repetitive strain injury) consists of chronically inflamed tendons. Current therapy reduces, but almost never totally relieves, the signs and symptoms of the underlying inflammatory process. Even if a problem goes away, it takes months of taking medicine daily, physical therapy, and markedly restricted activities.

The method described herein restores normal function instantly with complete resolution of signs and symptoms in the locations treated. The resolution is permanent, unless significant re-injury occurs. Thus, the cost of treatment is less. The method is safer than current therapies by avoiding contractures, adhesions, atrophy and other complications of the inflammation. The method also avoids gastritis, anemia, kidney damage, liver damage, hypertension, sodium retention, and a number of other problems associated with the current practice of treating this condition with NSAIDs (non-steroidal anti-inflammatory drugs). Summarized, these advantages are: efficacy, expediency, safety, decreased disability, and decreased cost.

The use of the medications locally enables the use relatively low dosage by avoid reliance on the circulatory system for delivery. Non-targeted areas receive minimal exposure to the medications. The benefits of this process are attained in one application, thus avoiding the time, expense, and side effects of multiple dosing. The rapid effect allows recipients to rapidly return to normal activities and therefore eliminate deconditioning and disuse atrophy. The method is relatively simple, inexpensive, fast, effective, and safe with few, if any, side effects when performed by a careful, trained professional with knowledge of anatomy.

The Method and its Components

Figure 15:
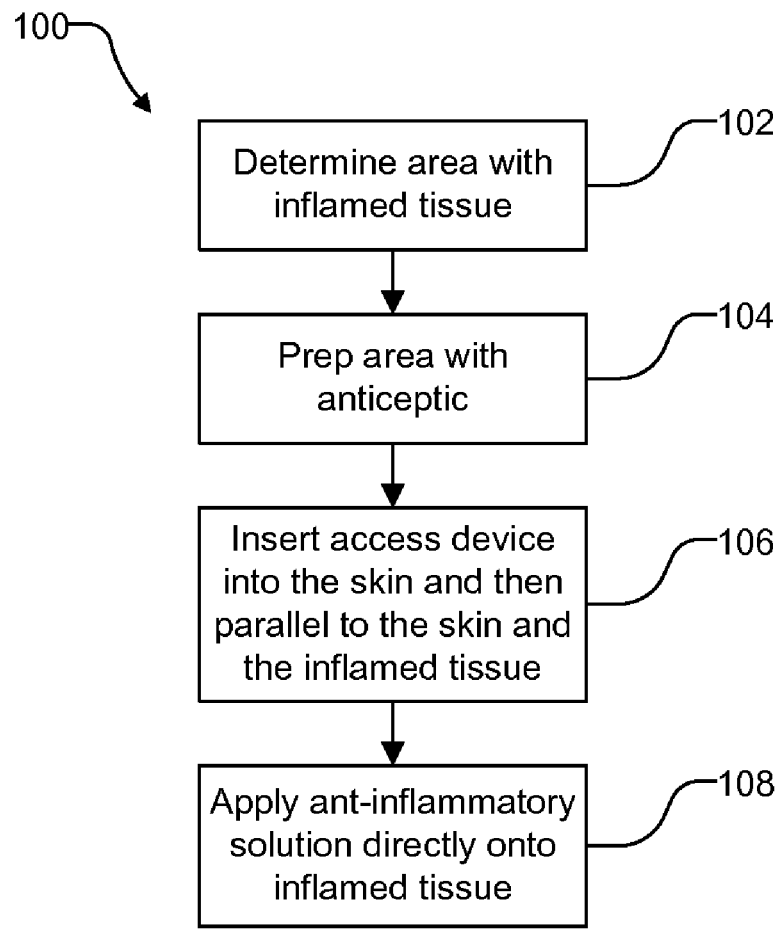
FIG. 15 is a flowchart of a method for treating inflamed tissues in one embodiment of the invention.

FIG. 1 illustrates the components or materials typically needed to treat inflamed subcutaneous tissues, such as tendons, muscles, ligaments, fascia, and nerves in one embodiment of the invention. FIG. 15 illustrates a method 100 for treating inflamed tissues in one embodiment of the invention.

Figure 2:
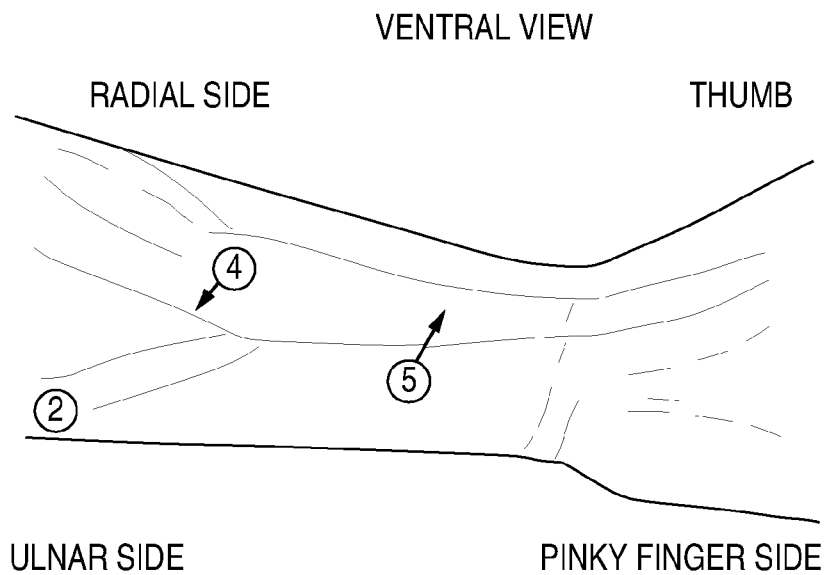
FIG. 2 illustrates areas of inflamed tissues that can be treated in on embodiment of the invention.
Figure 3:
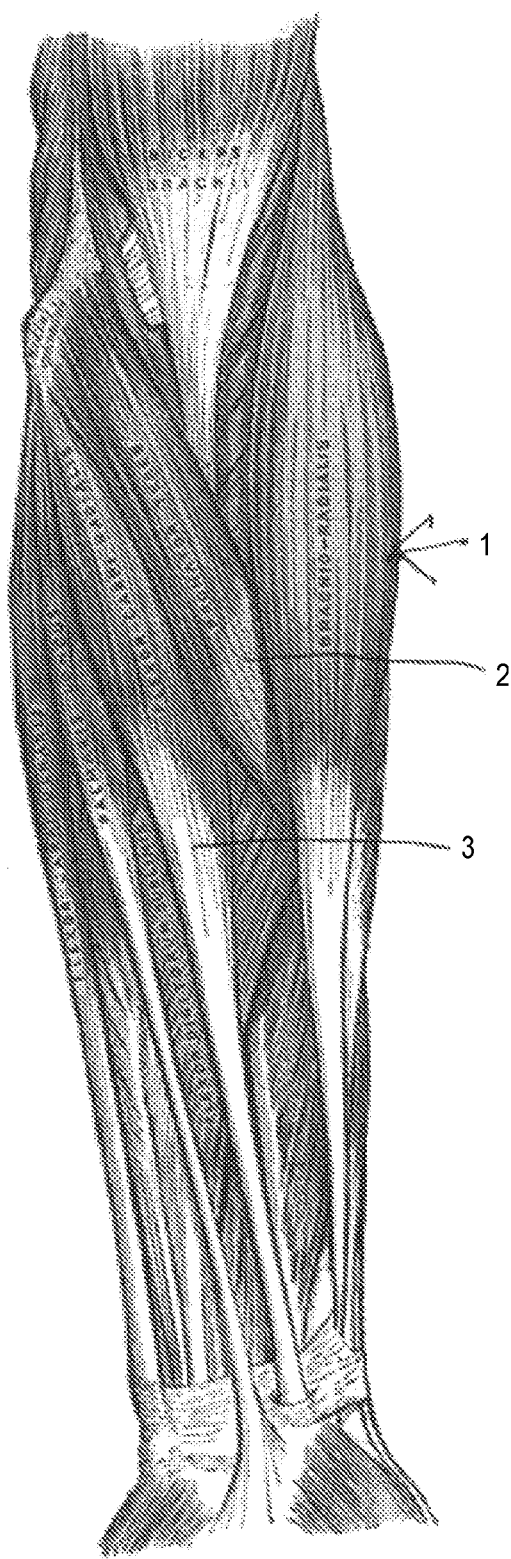
FIGS. 3 and 4 illustrate the first and the second layer of muscle under the skin.
Figure 4:
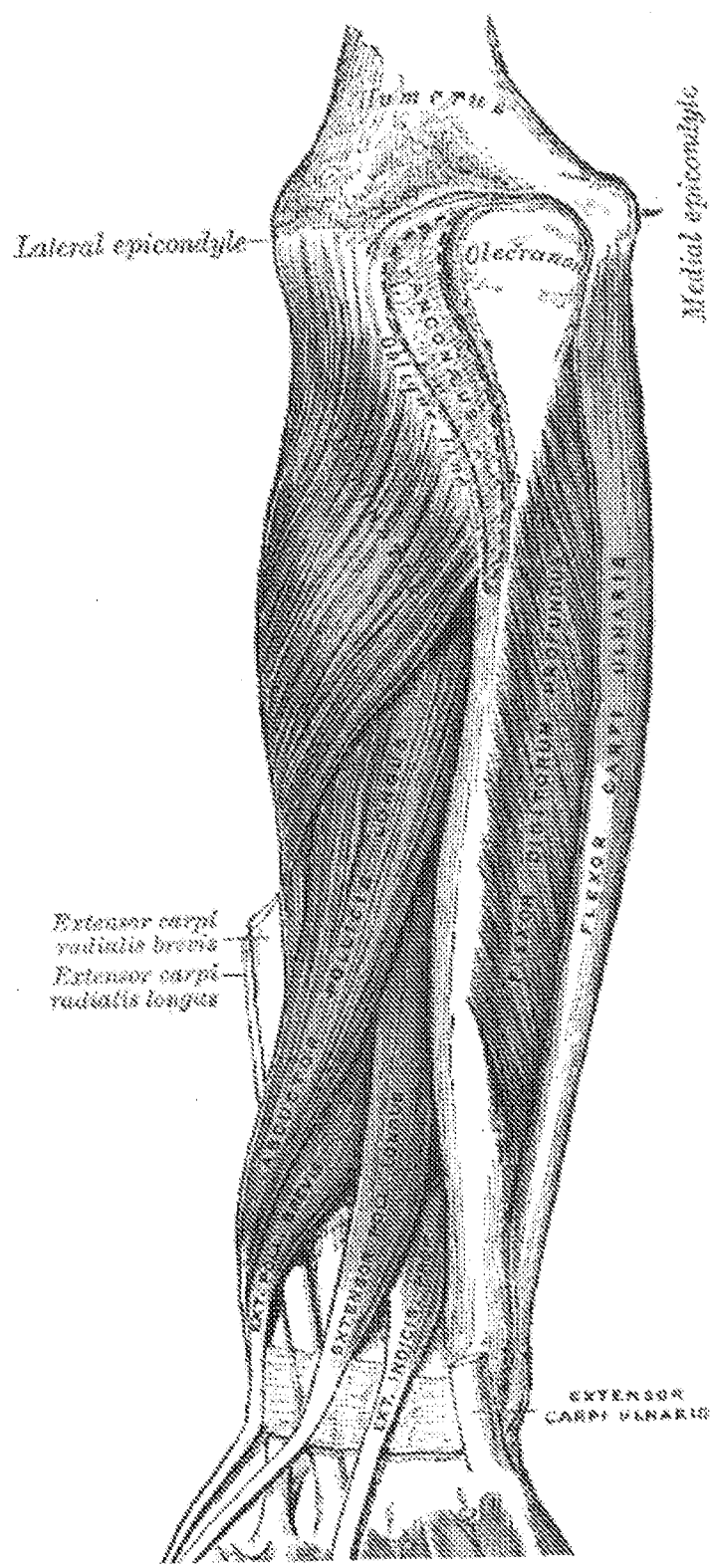

In step 102 (FIG. 15), the inflamed tissue to be treated is first located. FIG. 2 is a map of inflamed tissues (e.g., inflamed tendons) that can be treated. FIGS. 3 and 4 illustrate the first and the second layer of muscles under the skin of FIG. 2. A skilled clinician can use (1) medical history, (2) physical examination, (3) clinical testing, and (4) medical testing to determine the site of the problem. Medical history includes the mechanism of injury, type of pain (e.g., burning=neuropathic=inflammation of or near free nerve endings), and precipitative factors (e.g., determining what movement, position, or activity makes the condition worse). Physical examination includes visual inspection for swelling, erythema, and decreased motion, and physically inspection for palpation, heat, and tenderness. Clinical testing includes Finkelstein's, Tinnel's, and Phalen's. Furthermore, a "pinch test" in which the skin is pinched to find areas of hyperesthesia (a clinical sign of neuropathic pain) can also be used. Medical testing includes tracing many types of Nuclear Medicine isotopes that accumulate in inflammatory cells (e.g., gallium, technetium, and thallium). Ultrasound is a very sensitive method of diagnosing tendonitis. Thermography can show areas of inflammation based very sensitively and accurately based on the excessive heat given off by inflamed tissue.

In step 104 (FIG. 15), an applicator 12 (FIG. 1) is used to apply an antiseptic (e.g., Betadine®) to disinfect the site of the problem. Alcohol can also be used but its efficacy is questionable because it takes at least two minutes of exposure to kill bacteria. Step 104 is performed mainly as a placebo because skin infections secondary to injections with sterile needles and medications are extremely rare.

Figure 5:
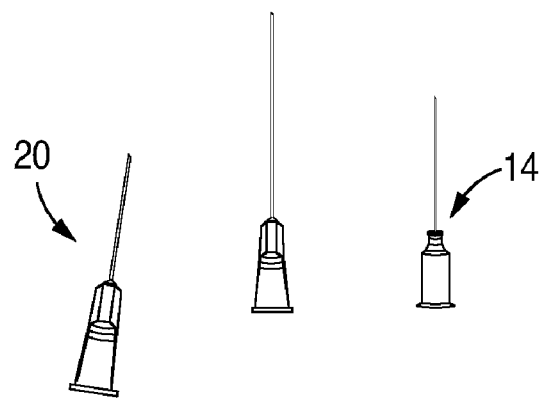
FIG. 5 illustrates a 1" 21-gauge hypodermic needle and a 1" 30-gauge hypodermic needle used in one embodiment of the invention.

In step 106 (FIG. 15), an access device 14 (FIGS. 1, 5, and 6) is used to access the inflamed tissue. In one embodiment, access device 14 is a 30-gauge hypodermic needle. Needle 14 is barely perceptible when penetrating the skin to most people. Needle 14 is also flexible, thereby allowing precise direction control and delivery of small amounts of medication. In other embodiments, access device 14 can be a trocar, a catheter, an endoscope, a scalpel, or any other tool or instrument that may be used for accessing subcutaneous structures.

In step 108 (FIG. 15), needle 14 is used to inject an anti-inflammatory solution. In one embodiment, the anti-inflammatory solution is a combination of a corticosteroid 16 (FIG. 1) and an anesthetic agent 18 (FIG. 1) is used. In one embodiment, corticosteroid 16 is a dexamethasone 4 mg/ml (e.g., a dexamethasone sodium phosphate injection) and anesthetic agent 18 is a 1% lidocaine (e.g., a lidocaine HCL injection). In one embodiment, dexamethasone 16 and lidocaine 18 injections are mixed in a ratio of 1 to 3 in volume. However, this ratio is subject to change based on future study.

In one embodiment, dexamethasone 4 mg/ml is selected for the following reasons.

It has a low viscosity. This allows the use of a small-bore needle. A 30-gauge needle cannot be used with almost all the other injectable corticosteroids on the market.

It is totally water soluble.

It is clear and colorless.

It has a short serum half-life of 3-4 hours.

It leaves no residual in treated tissue, and

It contains only one chemical with a potential to cause significant problems—disulfite used as a preservative causes allergies rarely.

It is a pure glucocorticoid.

It is relatively inexpensive.

It has been on the market since the early 1960's.

In one embodiment, a 1% lidocaine injection without epinephrine is selected for the following reasons.

It is widely used.

It is relatively inexpensive.

It has few side effects in low dosages.

It has a short half-life of 2 hours.

It has been on the market since the 1940's.

To make the anti-inflammatory solution, a 21-gauge needle 20 (FIG. 1) is used to draw corticosteroid 16 and anesthetic agent 18 from their containers into a syringe 22 (FIG. 1). The 21-gauge needle 20 is used for sterility and to avoid dulling or bending the 30-gauge needle 14. Needle 20 has a larger bore and is physically stronger so that medicine can be drawn up much faster. Instead of syringe 22, any other suitable reservoir or holding device capable of being attached to or used in conjunction with access device 14 can also be used. After the anti-inflammatory solution fills syringe 22, the 21-gauge needle 20 is replaced with the 30-gauge needle 14.

In one embodiment, a 3 cc syringe 22 is selected for the following reasons.

A syringe of this size allows treatment of about 24 inches of inflamed tendons, which is about the limit of tolerance for most patients.

It delivers a low dose of medication.

It offers significant improvement, low side effects, and lower cost per session than larger syringe.

When using a syringe and needle for subcutaneous injection, skin penetration seems best by using a very fine bore hypodermic needle (e.g., 1" 30 gauge). The recipient can barely feel the stick and the fine bore causes minimal tissue disruption. Furthermore, the fine needle is flexible enough to bend enabling aim in any direction, even around sharp curves.

Figure 6:
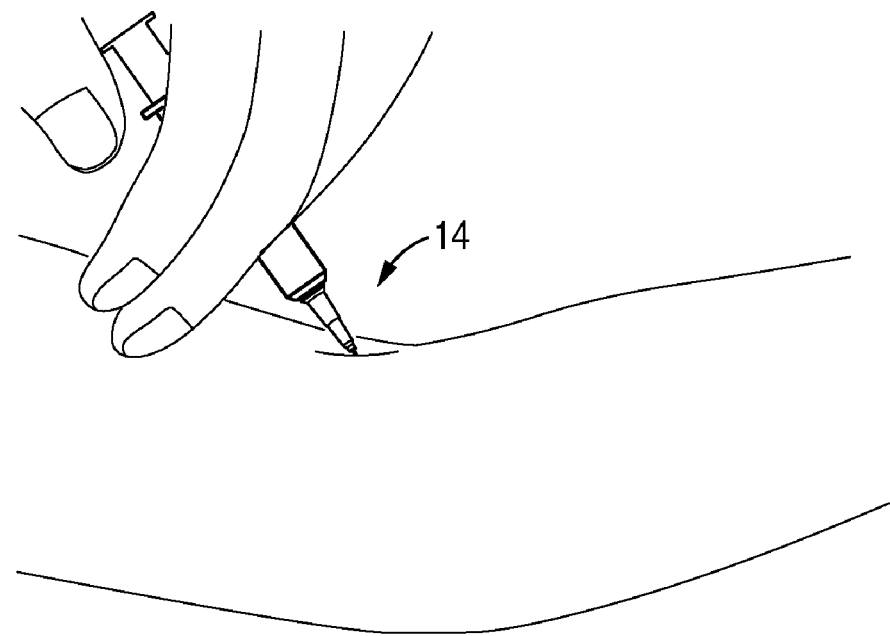
FIG. 6 illustrates a subcutaneous application of an anti-inflammatory solution to inflamed tissues in one embodiment of the invention.
Figure 7:
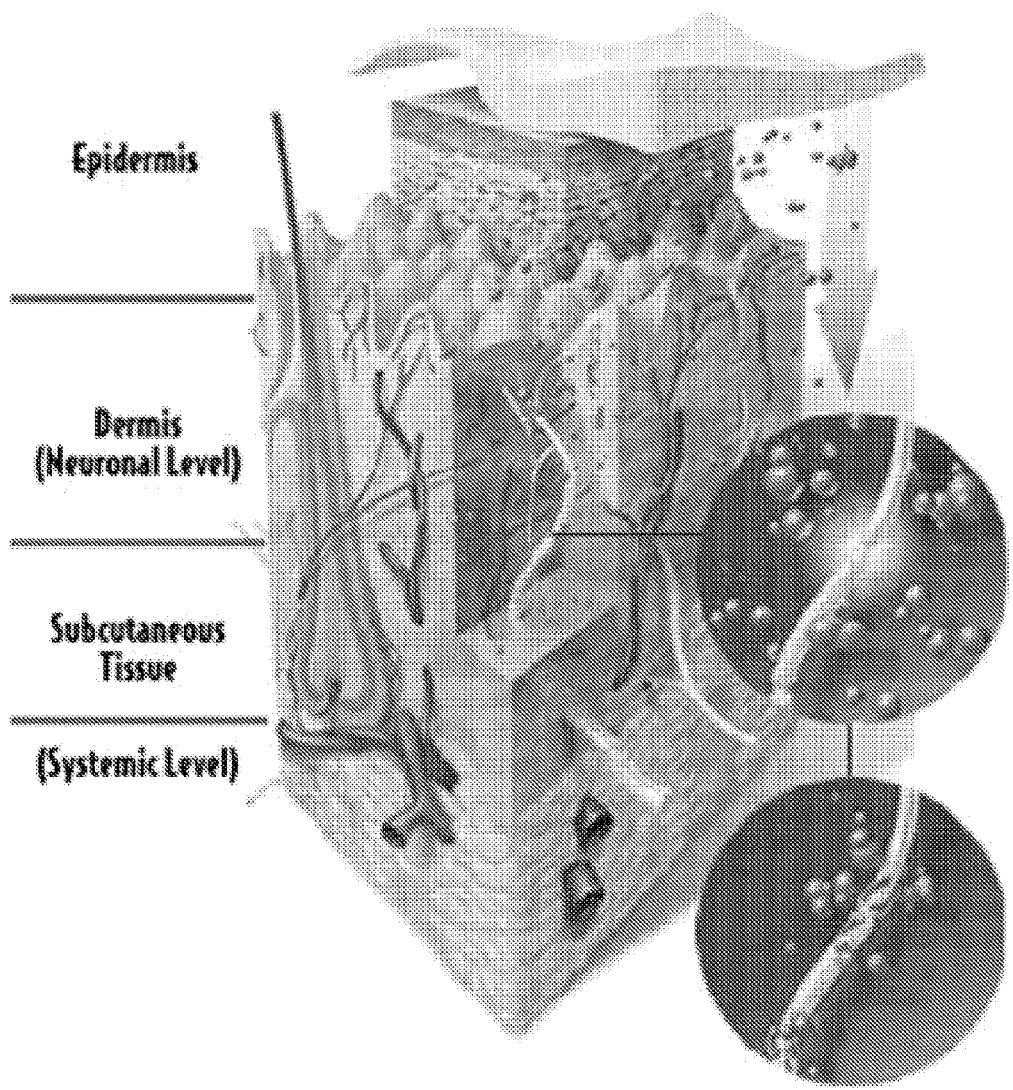
FIG. 7 illustrates the subcutaneous tissue.
Figure 8:
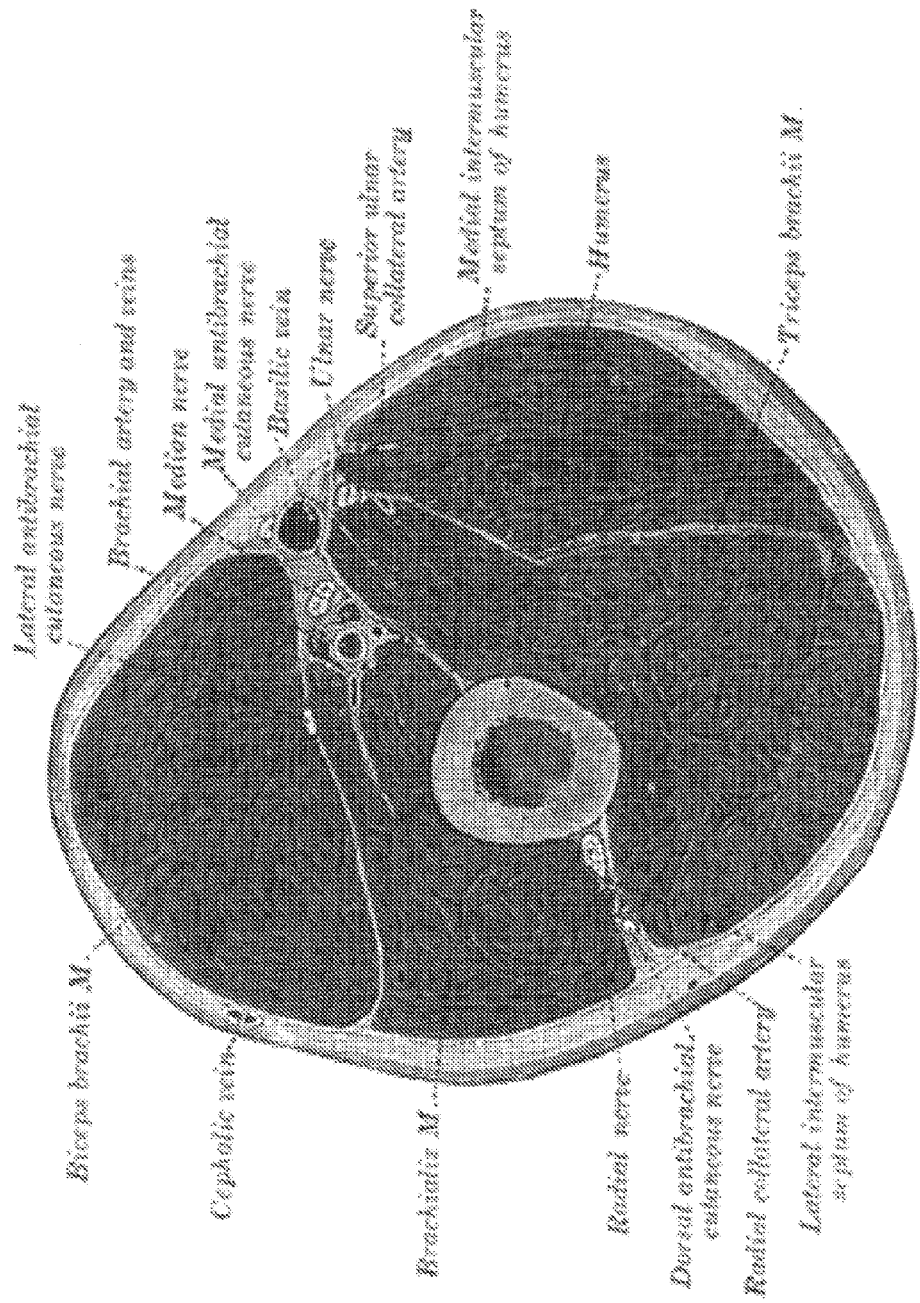
FIGS. 8, 9, 10, 11, 12, 13, and 14 illustrate the anatomy along the arm.
Figure 9:
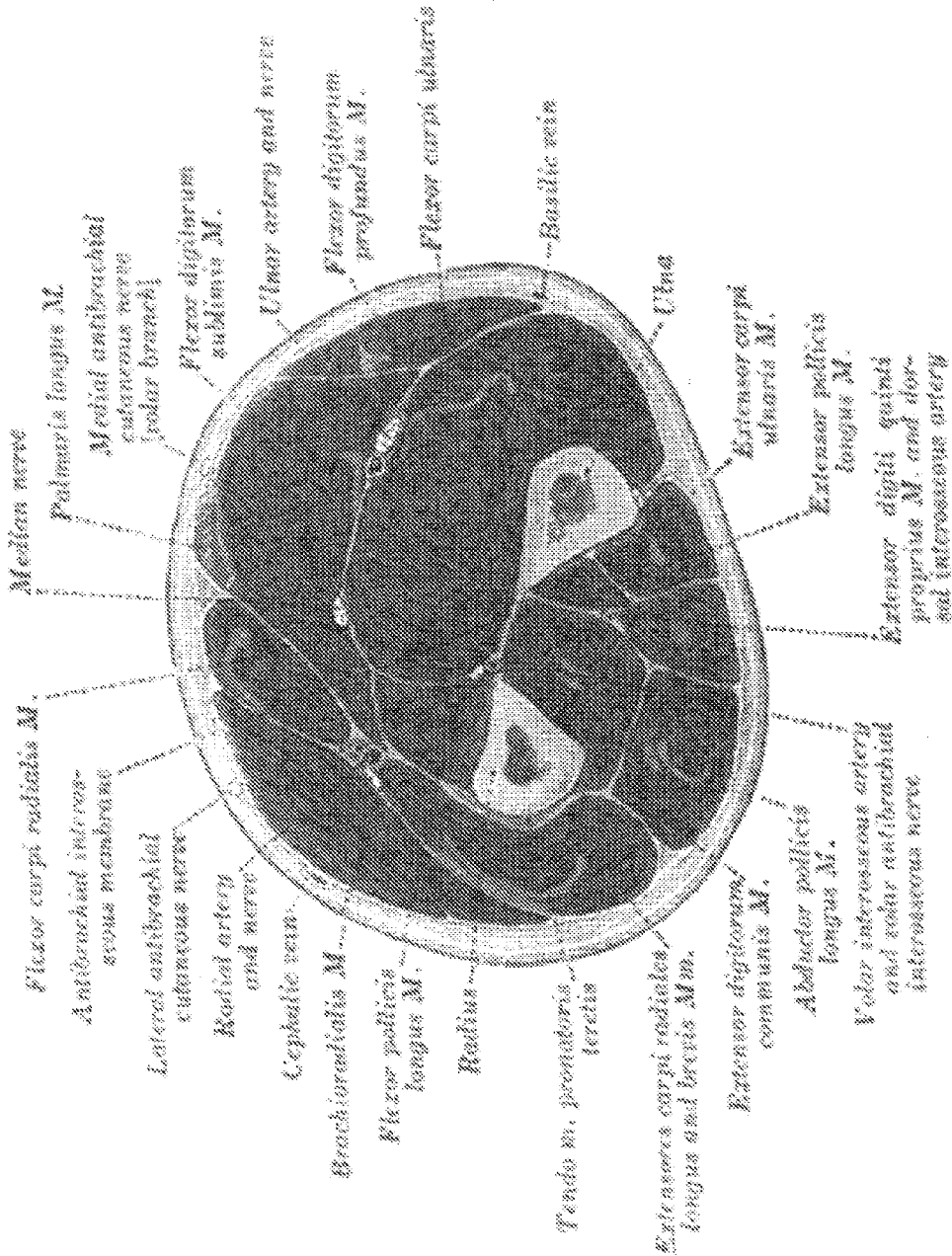
Figure 10:
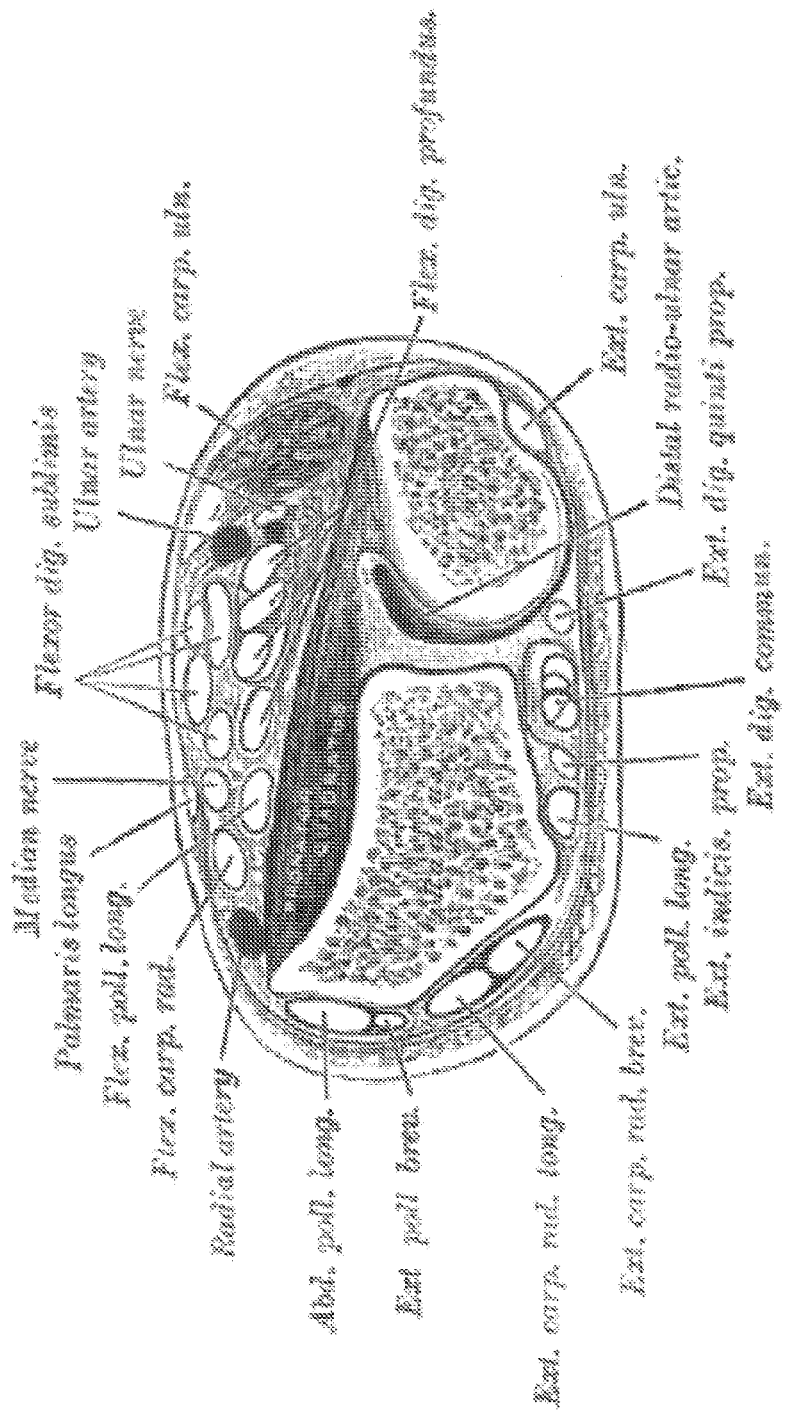
Figure 11:
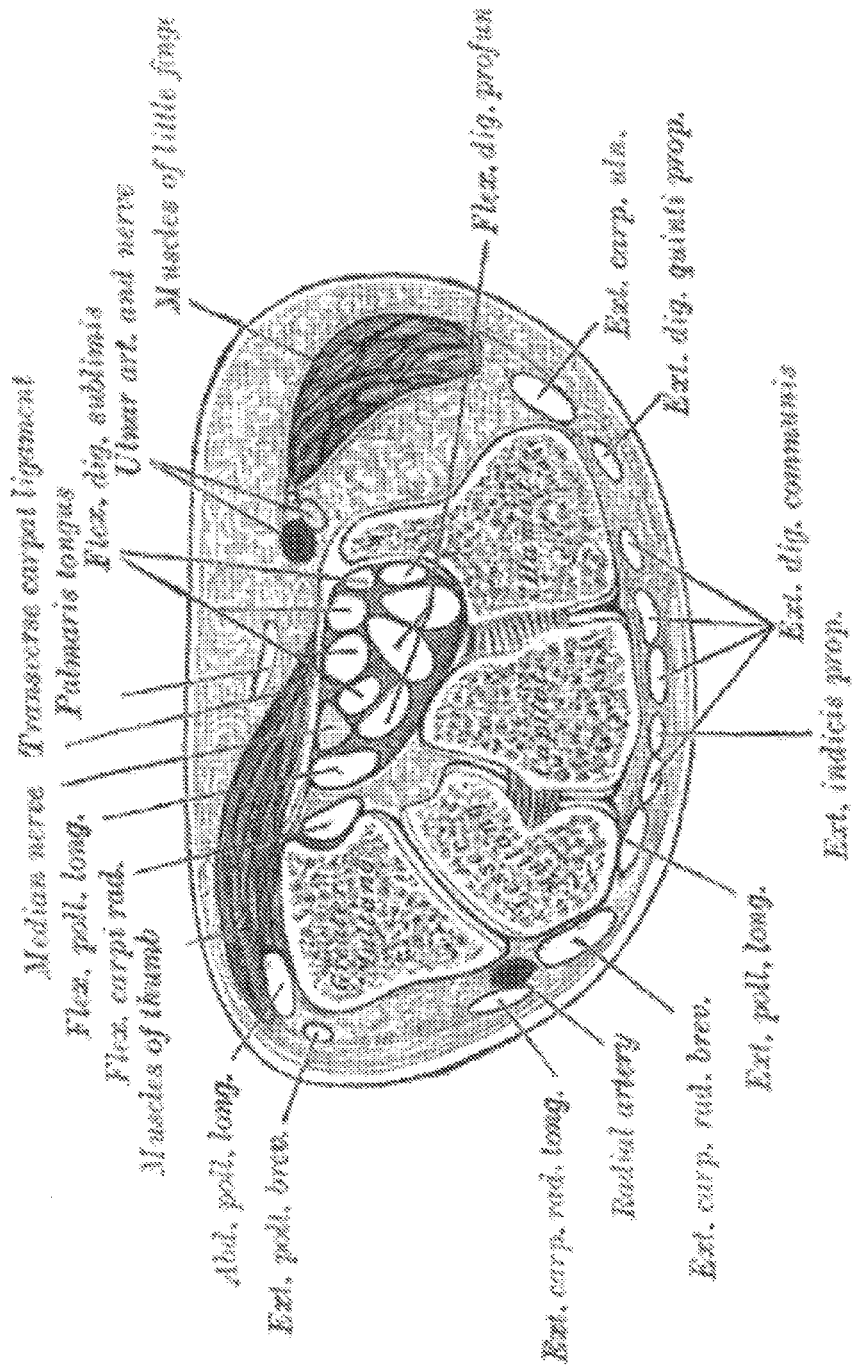
Figure 12:
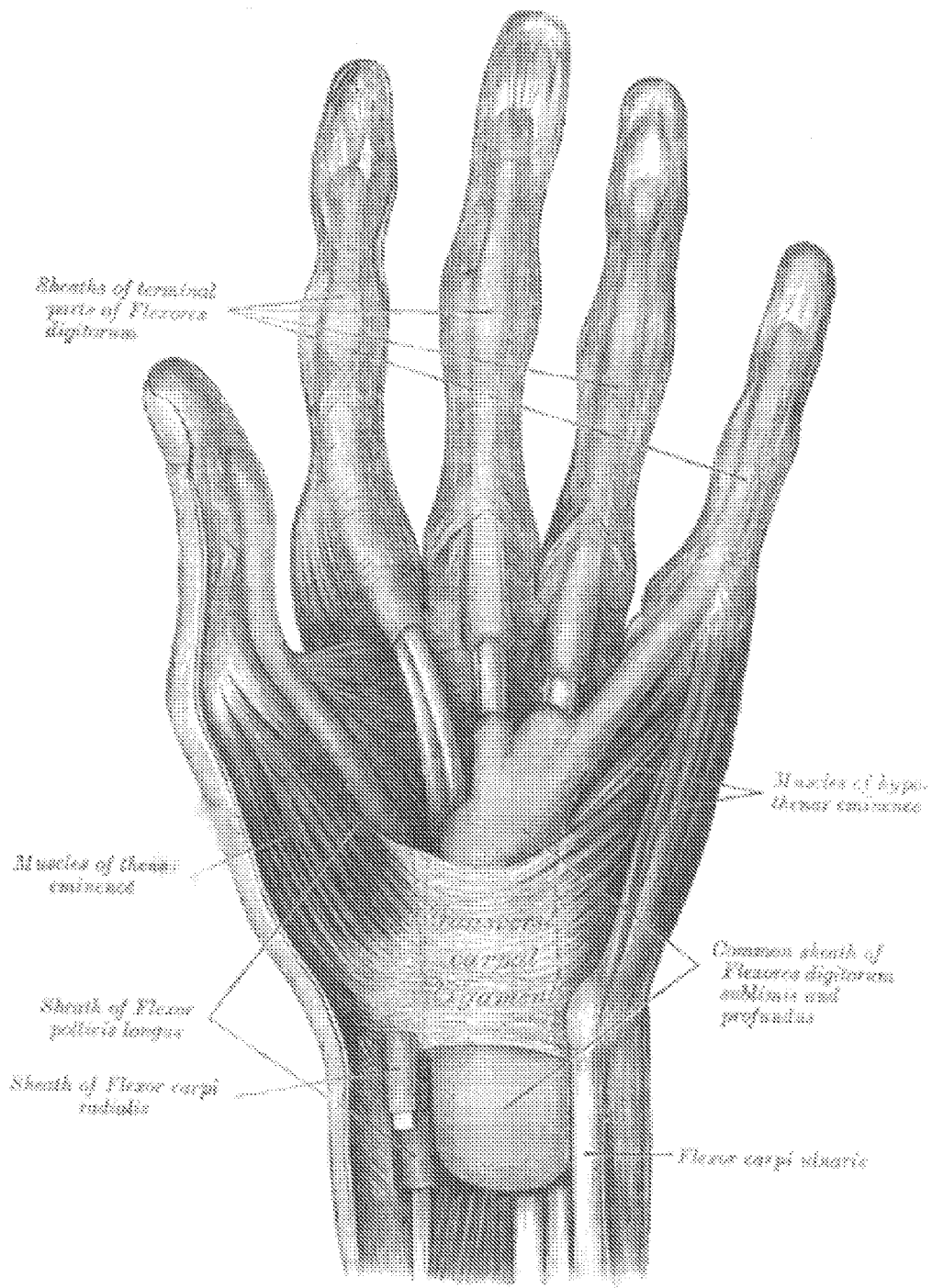
Figure 13:
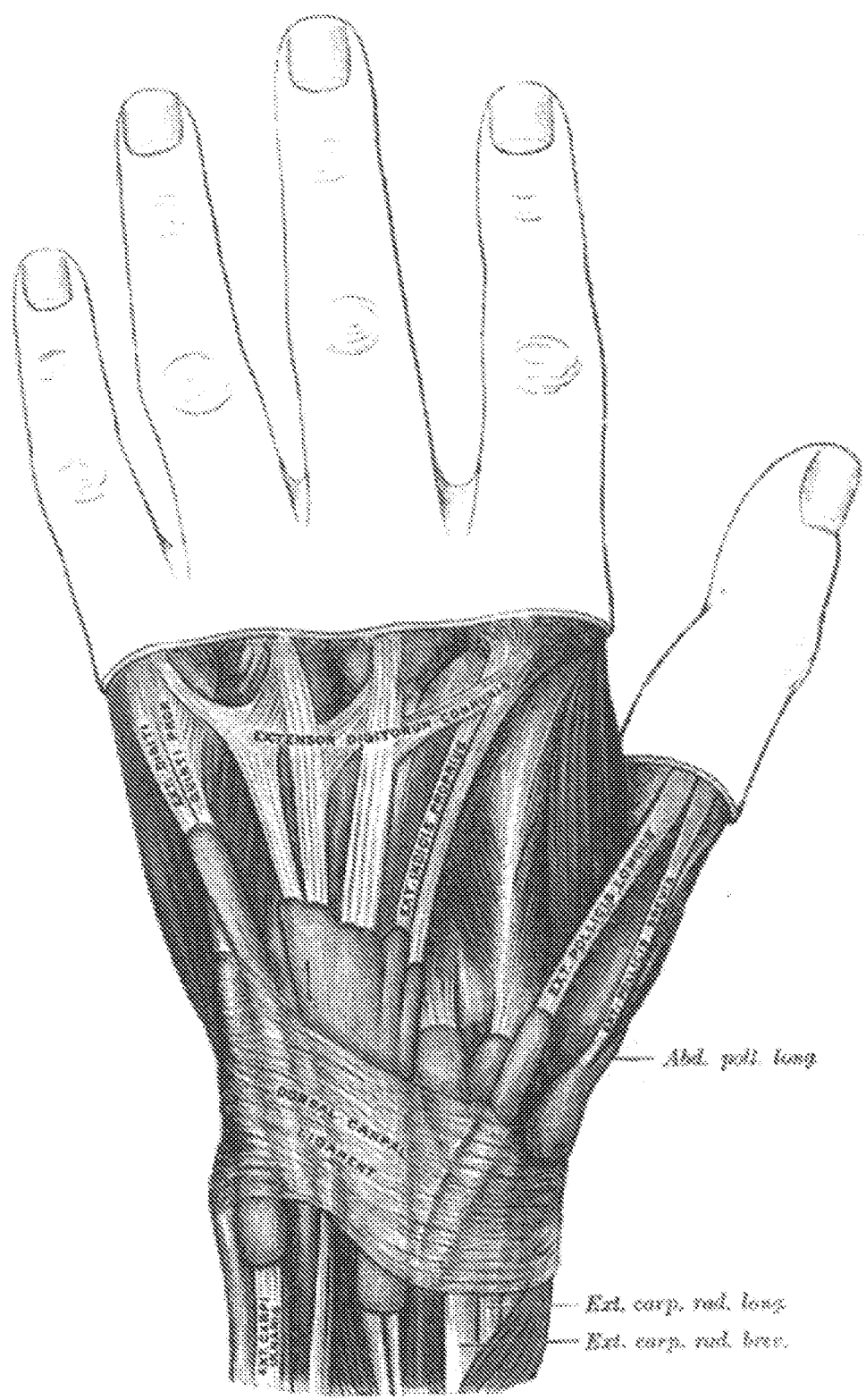
Figure 14:
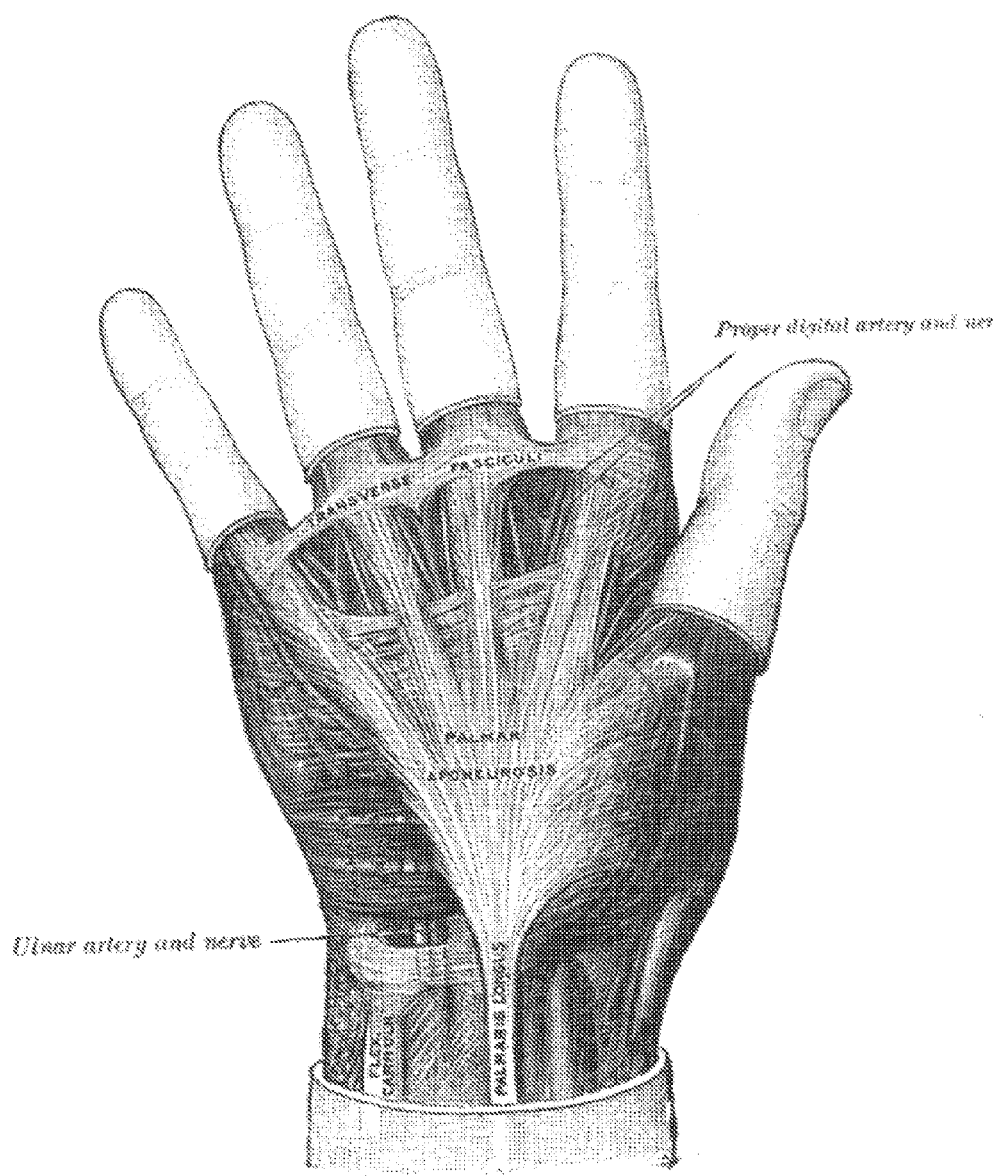

Needle 14 is inserted to a point adjacent to the inflamed area to be treated, and the medicines are delivered. As FIG. 6 shows, needle 14 is positioned at a 20° to 30° angle to the skin when penetrating the skin. The bevel of the needle should be facing down to avoid sticking structures immediately beneath the skin. Once the skin is penetrated, needle 14 is directed parallel to the skin and subcutaneous structures to be treated. The needle should traverse the subcutaneous tissue (illustrated in FIG. 7), below the dermis where nerves are situated. Therefore, the advancement of the needle should be painless. As the needle traverses the subcutaneous tissue, there should be slight traction on the plunger of the needle to alert the healthcare provider if a blood vessel is encountered.

In one embodiment, needle 14 is passed over the inflamed area, and then as needle 14 is withdrawn, the anti-inflammatory solution is sprayed in a fine mist or small droplets directly onto the surface of the inflamed tissue to be treated. It is important that the medication directly contacts the inflamed tissue because otherwise the technique less effective. For inflamed subcutaneous structures, such as tendons, ligaments, muscles, or inflammatory nodules, a 1" 30 gauge needle is used. For tendons, the dose is generally 8 inches of inflamed tendon per milliliter in one embodiment.

There is significant variation in the amount of pain, risk of complications, and amount of anatomic intricacy. FIGS. 8 to 14 show the increasing complexity of the anatomy as the picture progress from proximal to distal. Some areas have to be traversed with great care. The palm of the hand is especially difficult because of its sensitivity injections are more painful, there is limited space, which requires more accurate needle positioning and advancement; and injection of an excessive amount of fluid can cause pain from excessive pressure Flexor tendons of the hand are more delicate, are prone to more refractory inflammation and flexion contractures from stenosing or sclerosing tenosynovitis.

Carpal tunnel syndrome can be successfully treated by the method disclosed herein by injections in and around the carpal tunnel. The resolution of the inflammation results in the resolution of the swelling, which was putting pressure on the median nerve causing its dysfunction.

The method disclosed herein is also useful for treating trigger finger. Trigger finger is secondary to swelling as a result of inflammation of the flexor tendon of the involved finger as it passes through the A-1 pulley apparatus, or swelling of the apparatus itself. Treatment via the method disclosed herein can be curative.

The method disclosed herein may also be useful to prevent, reverse, or stabilize Dupetron's contractures if there is an inflammatory component, which are flexion contractures of usually the 3rd or long finger, the 4th or ring finger, or the 5th or pinky finger.

The Mechanism of Action of the Medications

The mechanism of action of the medications (i.e., the previously undiscovered synergism, for reducing inflammation) is unknown at present. The mechanisms of actions of the components of the medications (i.e., glucocorticoid steroids and anesthetics) are likewise not fully understood. Some of what is known is as follows.

Dexamethasone and other corticosteroids act through inhibition of prostaglandin and leukotriene synthesis, increased antioxidant activity, changing the patterns of polymorphonucleocyte margination and migration, interference with the action of cytokines and other transmitters of injury signals, and cell membrane stabilization.

Lidocaine and the other local anesthetics act by blocking sodium channels. Blocking sodium channels makes cell membranes more stable by inhibiting depolarization.

The mechanism of action for the synergistic effect of the combination of medications is unknown. Cell stabilization is common to both medications, and is no doubt of importance not only to preserve the cells under attack, but also to prevent the spread of inflammation by preventing the chemical messengers of injury from being released. Further investigations into the sodium channels will likely lead to more answers.

Alternative Methods

The access device, reservoir, and delivery system can vary considerably. Any device that gains direct access to the inflamed tissue to be treated and can hold and deliver the medications directly onto the surface or interior of an inflamed tissue will work.

Different types of corticosteroid medications can be used. Common injectable corticosteroids include Triamcinolone, Methylprednisolone, Dexamethasone, Cortisone, Hydrocortisone, Prednisolone tebutate, Bethamethasone (Celestone soluspan).

It is possible to substitute a different local anesthetic for lidocaine because all anesthetics work basically alike. Anesthetic agents vary primarily in their PKa's at various PHs. The PKa is the PH at which half the molecules are in the ionized form and half are in their unionized form. Only the unionized form can enter the cell, and once in the cell only the ionized form can block the sodium channels.

There are two broad classes of injectable local anesthetic: the esters and the amines. Esters were the first class of local anesthetic agents, and include cocaine, procaine, tetracaine, chloroprocaine and benzocaine. High allergenicity is a trait common to all ester based anesthetic. As a general rule if a patient is allergic to one ester anesthetic, they tend to be allergic to all of the esters.

Amines were invented later. They include Lidocaine, mepivicaine, Bupivicaine and all the other commonly used anesthetics. They all have the advantage of very low allergenicity. Allergies to these drugs are very rare. The vast majority of patients who are allergic to local anesthetics suffer only temporary generalized itching and skin rash when getting local anesthetic injections.

Table 1 shows common local anesthetics with their maximum doses and half-lives.

TABLE 1

| Anesthetic | Max dose Mg/Kg | Half-life in minutes |
| --- | --- | --- |
| Articaine | 7.0 | 20 |
| Mepivicaine 2% | 6.6 (4.5) | 115 |
| Etidocaine | 8.0 | 155 |
| Lidocaine | 7.0 (4.4) | 90 |
| Prilocaine | 8.0 (6.0) | 90 |
| Bupivicaine | 1.3 | 210 |

There are three amide anesthetic agents, which are most likely to be reasonable alternatives to lidocaine:

Bupivicaine, which is formulated in a 0.5% solution with a vasoconstrictor.

Prilocalne, which is formulated in a 4% solution.

Articaine, which is formulated in a 4.0% solution with vasoconstrictor.

The method disclosed herein may also work on skin, so that topical steroids and anesthetic can also be used.

Complications and Side Effects

The patient can experience serious pain during the injection if the needle hits a nerve or if the needle directly injects into a nerve, blood vessel, tendon, or the periostium of bone. However, most injections are not especially painful. The majority of the pain sensors are located in the surface epidermal layer. The method disclosed herein is designed to allow needle penetration with the least trauma to known existing structures under the skin. Unfortunately, variations in anatomy and the proximity of targeted tissues being treated makes hitting these structures a possibility. The use of small bore needles, slow advancement of the needle into areas, which are not previously numbed, and listening to the patient and halting immediately on any complaints minimizes this problem. Even if these structures are hit, the only problem is transient pain, especially if a vasoconstrictor is not used. The exception is a nerve, which may loose function.

Almost all problems with steroids result from chronic use. Steroids as used in the method disclosed herein are not expected to suppress ACTH (Adrenocorticotropic Hormone) or affect adrenal function, interfere with bone metabolism, fat metabolism, cause skin changes, mental changes, or make anyone steroid dependent. Short-term steroid use is very safe. There have been rare incidents of localized fat atrophy, skin hypopigmentation, thinning of the skin under the site of injection, and Achilles tendon rupture. These problems occur almost exclusively with long acting steroids, such as DepoMedrol.

Problems with anesthetics have been previously discussed.

It is unknown how and why the combination of the medications, when applied directly to the inflamed tissue, is supra additive and synergistic, thereby causing a much more favorable, immediate, dramatic and permanent response. However, the safety of the individual components is known. Both medications have been time tested. Lidocaine, trade name Xylocaine®, was the first modern local anesthetic agent. It was invented and has been used since the 1940s. Dexamethasone has been used since the early 1960's. Both medication components have had extensive use. It is estimated that the average dentist administers about 1750 injections of local anesthesia each year, in addition to medical and veterinary usage. Corticosteroids are probably the most widely used medicine, in the practice of medicine, especially dermatology. Both medication components have short half-lives, i.e., are in the body only a short time. Lidocaine has a half-life of roughly 2 hours. This means, according to the laws of pharmacokinetics, that lidocaine will be essentially eliminated from the body in 10 hours or 5 half-lives. Dexamethasone is very water-soluble and starts getting washed away almost immediately. The serum half-life of dexamethasone is 3-4 hours.

Both agents have high therapeutic indices (i.e., the difference between the lethal dose and the dose used to treat a given condition). The average 150-pound adult in good health can tolerate between 400 and 600 mg of these agents. A 2% solution contains 20 mg of anesthetic agent per milliliter; a 1% solution has 10 mg/ml. These doses mentioned above are not considered lethal (maximum doses for common anesthetics are shown in Table 1 above). They are merely the doses at which some people begin to feel toxic systemic effects from the drugs, which may include Central Nervous System effects of sedation, light headedness, slurred speech, shivering or twitching or, in rare cases, seizures; or cardiovascular effects such as hypotension. The incidence of toxicity to local anesthetics in an adult patient setting is extremely rare, and generally is secondary to an unusual patient with physiologic abnormalities.

Allergic Reactions are rare with both medication components. Dexamethasone and other steroids are used to treat allergic reactions. Dexamethasone is made with a bisulfite as a preservative, so a very rare patient might have problems if the have a sulfite allergy. Allergic reactions to the amide anesthetics are rare, as previously discussed.

Various other adaptations and combinations of features of the embodiments disclosed are within the scope of the invention. Numerous embodiments are encompassed by the following claims.

What is claimed is:

1. A method for treating an inflamed tissue, comprising:
   penetrating the skin with an access device;
   once the access device is below the skin, directing the access device into the subcutaneous tissue and parallel to the inflamed tissue; and
   spraying a solution from the access device while withdrawing the access device so the solution is applied directly on a surface of the inflamed tissue, wherein the solution comprises a corticosteroid and an anesthetic agent.

2. The method of claim 1, wherein the corticosteroid comprises a 4 mg/ml dexamethasone injection and the anesthetic agent comprises a 1% lidocaine injection.

3. The method of claim 2, wherein the solution comprises a 1 to 3 ratio of the dexamethasone injection to the lidocaine injection.

4. The method of claim 1, wherein the access device is selected from the group consisting of a hypodermic needle, a trocar, a catheter, an endoscope, and a scalpel.

5. The method of claim 1, wherein said directing the access device further comprises:
   directing the access device parallel to and past the inflamed tissue.

6. The method of claim 1, wherein the corticosteroid is selected from the group consisting of dexamethasone, triamcinolone, methylprednisolone, cortisone, hydrocortisone, prednisolone tebutate, and bethamethasone.

7. The method of claim 1, wherein the anesthetic agent is selected from the group consisting of lidocaine, bupivicaine, prilocalne, and articaine.

8. A method for treating an inflamed tissue, comprising:
   penetrating the skin with an access device;
   once the access device is below the skin, directing the access device into the subcutaneous tissue and parallel to the inflamed tissue; and
   spraying a solution from the access device while withdrawing the access device so the solution is applied directly on a surface of the inflamed tissue.

9. The method of claim 8, wherein said directing the access device further comprises directing the access device parallel to and past the inflamed tissue.

10. The method of claim 9, wherein the solution comprises a corticosteroid and an anesthetic agent.

* * * * *